United States Patent
Kinoshita et al.

(10) Patent No.: US 6,514,606 B2
(45) Date of Patent: Feb. 4, 2003

(54) PRESSURE-SENSITIVE ADHESIVE SHEET FOR SKIN ADHESION AND FIRST-AID ADHESIVE PLASTER USING THE SAME

(75) Inventors: Takashi Kinoshita, Ibaraki (JP); Yasuyuki Sasaki, Ibaraki (JP); Masayoshi Kuniya, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/394,707

(22) Filed: Sep. 13, 1999

(65) Prior Publication Data

US 2002/0064651 A1 May 30, 2002

(30) Foreign Application Priority Data

Sep. 30, 1998 (JP) .......................................... 10-277703

(51) Int. Cl.$^7$ ............................................... B32B 27/30
(52) U.S. Cl. ........................ 428/343; 428/522; 428/523; 524/394; 524/398; 524/399; 524/400; 524/450; 602/42; 602/43; 602/46; 602/54; 602/58
(58) Field of Search .................................. 428/343, 522, 428/523; 524/394, 398, 400, 399, 450; 602/42, 43, 46, 54, 58

(56) References Cited

U.S. PATENT DOCUMENTS

| | | | |
|---|---|---|---|
| 4,670,490 A | * | 6/1987 | Yoshida et al. ............. 524/115 |
| 5,561,182 A | * | 10/1996 | Baker et al. ................ 524/394 |
| 5,800,919 A | * | 9/1998 | Peacock et al. ........ 428/355 AC |
| 6,077,986 A | * | 6/2000 | Hilston et al. ................ 602/54 |
| 6,136,900 A | * | 10/2000 | Kuhn et al. .................... 524/99 |

FOREIGN PATENT DOCUMENTS

| | | |
|---|---|---|
| JP | 7-188490 | 7/1995 |
| JP | 9-316403 | 12/1997 |
| JP | 10-14973 | 1/1998 |
| JP | 10-36784 | 2/1998 |

OTHER PUBLICATIONS

Sekkai to Sekko (Lime and Gypsum) vol. 187, pp. 47–53 (1983).

* cited by examiner

Primary Examiner—James J. Seidleck
Assistant Examiner—Melanie Bissett
(74) Attorney, Agent, or Firm—Sughrue Mion, PLLC

(57) ABSTRACT

A pressure-sensitive adhesive sheet for skin adhesion in which an adhesive force of the pressure-sensitive adhesive on the backing film does not lower greatly even with the lapse of long term and the initial adhesive force is substantially maintained, and a first-aid adhesive plaster using the same are disclosed. The pressure-sensitive adhesive sheet for skin adhesion comprises a backing film and a pressure-sensitive adhesive layer for skin adhesion formed on one side of the backing film, wherein the backing film comprises about 40 to about 70 parts by weight of a polyester plasticizer having a number average molecular weight of about 1,500 to about 3,000, an appropriate amount of a stabilizer comprising at least one metallic soap selected from the group consisting of fatty acid calcium, fatty acid zinc and fatty acid barium, and about 0.1 to about 1.0 part by weight of hydrotalcite per 100 parts by weight of a vinyl chloride polymer.

26 Claims, No Drawings

PRESSURE-SENSITIVE ADHESIVE SHEET FOR SKIN ADHESION AND FIRST-AID ADHESIVE PLASTER USING THE SAME

BACKGROUND OF THE INVENTION

1. Field of the Invention

The present invention relates to a pressure-sensitive adhesive sheet for skin adhesion comprising a backing film comprising a flexible vinyl chloride resin, and a pressure-sensitive adhesive layer provided on one side of the backing film, and its use. More particularly, the invention relates to a pressure-sensitive adhesive sheet for skin adhesion that an adhesive force of the pressure-sensitive adhesive on the backing film does not lower greatly even with the lapse of long term and substantially maintains the initial adhesive force, and to its use, for example, a use as a first-aid adhesive plaster.

2. Description of the Related Art

Conventionally, a pressure-sensitive adhesive sheet for skin adhesion comprising a flexible backing film having provided thereon a pressure-sensitive adhesive layer has been used as a dressing, a bandage or the like, and has also been widely used in homes as a first-aid adhesive plaster by providing an absorbent pad such as gauze at a central region on a surface of the pressure-sensitive layer. Further, an adhesive drug sheet for skin adhesion comprising a backing film having provided thereon a layer comprising a pressure-sensitive adhesive containing various drugs is used for various medical uses. Conventionally, a film comprising a so-called flexible vinyl chloride resin has widely been used as the backing film for such a pressure-sensitive adhesive sheet for skin adhesion from the points that it is flexible, has good adaptability to skin, and has excellent printability. In such a flexible vinyl chloride resin, a combination of a fatty acid calcium-fatty acid zinc type stabilizer and an epoxidized soybean oil has generally been used as a stabilizer from the standpoint of safety. However, when an acrylic pressure-sensitive adhesive, for example, is coated on a backing film comprising such a vinyl chloride resin to prepare an adhesive plaster, an adhesive force of the backing film decreases with the passage of time. Thus, where the adhesive force of the pressure-sensitive adhesive decreases, even if the adhesive plaster is adhered to a skin, an edge of the adhesive plaster lifts from the skin, and in some cases, the adhesive plaster peels off from the skin. As a result, the adhesive plaster may not exhibit the function as a first-aid adhesive plaster.

SUMMARY OF THE INVENTION

As a result of extensive investigations to overcome those problems in the conventional pressure-sensitive adhesive sheet for skin adhesion using a vinyl chloride resin film as a backing film, the inventors have found that in the conventional vinyl chloride resin film, an epoxidized soybean oil compounded as a plasticizer migrates from the backing film to the pressure-sensitive adhesive layer with the passage of time, thereby crosslinking or curing an acrylic pressure-sensitive adhesive, for example, and as a result, the pressure-sensitive adhesive loses its initial adhesive force, so that the adhesive force lowers with the passage of time.

Based on the above-described finding, the inventors also have made further investigation and found that when a polyester plasticizer is used as a plasticizer in place of the epoxidized soybean oil, and a combination of a metallic soap and a hydrotalcite is used as a stabilizer, a film produced by calendering has an excellent heat stability, and also found that when the film thus obtained is used as the backing film, and a pressure-sensitive adhesive is applied to one side of the backing film to form a pressure-sensitive adhesive sheet for skin adhesion, the plasticizer does not migrate into the pressure-sensitive adhesive layer, and the pressure-sensitive adhesive sheet for skin adhesion can substantially maintain the initial adhesive force even with the lapse of long term. The present invention has been completed based on this finding.

Accordingly, one object of the present invention is to provide a pressure-sensitive adhesive sheet for skin adhesion including a backing film that has an excellent heat stability during its production by calendering and a pressure-sensitive adhesive layer coated on one side of the backing film, a pressure-sensitive adhesive in the adhesive layer does not lose adhesive force greatly so that the initial adhesive force is substantially maintained.

Another object of the present invention is to provide a first-aid adhesive plaster using the pressure-sensitive adhesive sheet for skin adhesion.

According to a first aspect, the present invention provides a pressure-sensitive adhesive sheet for skin adhesion, which comprises a backing film and a pressure-sensitive adhesive layer for skin adhesion formed on one side of the backing film, wherein the backing film comprises: 100 parts by weight of a vinyl chloride polymer; about 40 to about 70 parts by weight of a polyester plasticizer having a number average molecular weight of about 1,500 to about 3,000; a stabilizing effective amount of a stabilizer comprising at least one metallic soap selected from the group consisting of fatty acid calcium, fatty acid zinc and fatty acid barium; and about 0.1 to about 1.0 part by weight of hydrotalcite.

Here, the vinyl chloride polymer may be at least one polymer selected from a polymer of vinyl chloride alone and copolymers of vinyl chloride and an ethylenically unsaturated hydrocarbon having 2 to 4 carbon atoms.

The vinyl chloride polymer may be at lest one polymer selected from the group consisting of polyvinyl chloride and vinyl chloride/ethylene copolymers and vinyl chloride/vinyl acetate copolymer.

The vinyl chloride polymer may preferably have an average degree of polymerization of about 500 to about 1,500.

The polyester plasticizer may comprise a polyester obtained from an aliphatic or aromatic dicarboxylic acid having 2 to 10 carbon atoms and a glycol having 2 to 10 carbon atoms.

The polyester plastercizer may preferably have a number average molecular weight of about 1,500 to about 3,000.

The metallic soap may preferably be a combination of a fatty acid calcium and a fatty acid zinc.

The fatty acid in the metallic soap may be a saturated or unsaturated fatty acid having 12 to 20 carbon atoms.

The metallic soap may be in an amount of about 0.5 to about 2.5 parts by weight per 100 parts by weight of the vinyl chloride polymer.

The pressure-sensitive adhesive may preferably be an acrylic pressure-sensitive adhesive.

The acrylic pressure-sensitive adhesive may comprise a polymer comprising an alkyl acrylate having 4 to 12 carbon atoms in the alkyl moiety as a main monomer component.

The acrylic pressure-sensitive adhesive may further comprise at least one vinyl ester selected from the group consisting of alkyl (meth)acrylates having 1 to 3 carbon atoms in the alkyl moiety, vinyl acetate and N-methyl-2-pyrrolidone.

The acrylic pressure-sensitive adhesive may preferably comprise an acrylic pressure-sensitive adhesive that contains at least one of a hydroxyl group and a carboxyl group.

The acrylic pressure-sensitive adhesive may comprise a copolymer comprising an alkyl acrylate ester as a main monomer component and an hydroxyalkyl (meth) acrylate or (meth) acrylic acid as a comonomer copolymerizable therewith.

According to a second aspect, the present invention provides a first-aid adhesive plaster comprising the above-mentioned pressure-sensitive adhesive sheet for skin adhesion and an absorbent pad provided on a central region on a surface of the pressure-sensitive adhesive layer.

As described above, the pressure-sensitive adhesive sheet for skin adhesion according to the present invention comprises a backing film comprising a flexible vinyl chloride resin having compounded therewith a polyester plasticizer as a plasticizer, and hydrotalcite together with a metallic soap as a stabilizer, and a pressure-sensitive adhesive layer provided on one side of the backing film, and also the first-aid adhesive plaster of the present invention uses such a pressure-sensitive adhesive sheet for skin adhesion, so that the pressure-sensitive adhesive does not show a great decrease in adhesive force even after the lapse of long time, and substantially maintains the initial adhesive force.

Other objects and advantages of the present invention will become apparent from the detailed description to follow taken in conjunction with the appended claims.

DETAILED DESCRIPTION OF THE INVENTION

The present invention is described in detailed below.

The vinyl chloride polymer that can be used in the present invention includes a homopolymer of vinyl chloride, i.e., polyvinyl chloride, and copolymers of vinyl chloride and various comonomers. Examples of the comonomer include ethylenically unsaturated hydrocarbons having 2 to 4 carbon atoms, such as ethylene, propylene, vinyl acetate, acrylic acid, acrylic acid ester, methacrylic acid, methacrylic acid ester, maleic acid, fumaric acid, acrylonitrile, vinylidene chloride, styrene, etc. The alkyl moiety in the acrylic acid esters and methacrylic acid esters have 1 to 10 carbon atoms and specific examples thereof include methyl, ethyl, propyl, butyl, pentyl, hexyl, octyl, nonyl, decyl, etc. Those comonomers can be used alone or as mixtures of two or more thereof. Preferred examples of the vinyl chloride polymer used in the present invention include polyvinyl chloride, vinyl chloride/ethylene copolymer, and vinyl chloride/vinyl acetate copolymer. Of those, polyvinyl chloride is more preferably used in the present invention. In general, those vinyl chloride polymers have an average degree of polymerization of about 500 to about 1,500, and preferably about 700 to about 1,300. If the average degree of polymerization is less than about 500, mechanical strength is insufficient while with an average degree of polymerization of exceeding about 1,500, the compatibility with plasticizers tends to be decreased.

A plasticizer, a stabilizer and the like are compounded with the vinyl chloride polymer to prepare a resin composition. The resin composition is then subjected to calendering to form a film comprising a flexible vinyl chloride resin, thereby obtaining a backing film for use in the pressure-sensitive adhesive sheet for skin adhesion according to the present invention.

According to the present invention, a polyester plasticizer is used in place of the conventional epoxidized soybean oil. The polyester plasticizer used in the present invention comprises, for example, a polyester obtained by polycondensation of an aliphatic or aromatic dicarboxylic acid having 2 to 10 carbon atoms, such as adipic acid, azelaic acid, sebacic acid, phthalic acid, isophthalic acid, terephthalic acid, and a glycol having 2 to 10 carbon atoms, such as ethylene glycol, propylene glycol, butylene glycol, neopentyl glycol. In particular, according to the present invention, the polyester plasticizer having a number average molecular weight of about 1,500 to about 3,000 is used in an amount of about 40 to about 70 parts by weight, preferably about 45 to about 65 parts by weight, per 100 parts by weight of the vinyl chloride polymer.

If the number average molecular weight of the polyester plasticizer is less than about 1,500, the plasticizer migrates from the backing film it is compound in to the pressure-sensitive adhesive layer, and this results in a decrease in adhesive force of the pressure-sensitive adhesive with the passage of time. On the other hand, if the number average molecular weight of the polyester plasticizer is more than about 3,000, such a polyester plasticizer has poor compatibility with the vinyl chloride polymer, making it difficult to produce the backing film by calendering, and also the plasticizer bleeds out in the backing film obtained, decreasing the adhesive force of the pressure-sensitive adhesive to the backing film.

Particularly, the amount of the polyester plasticizer compounded is generally about 40 to about 70 parts by weight per 100 parts by weight of the vinyl chloride polymer such that the backing film for the pressure-sensitive adhesive sheet for skin adhesion has an appropriate modulus of elasticity that is flexible and adaptable to a skin.

In the vinyl chloride resin film as the backing film for use in the pressure-sensitive adhesive sheet for skin adhesion, a metallic soap has conventionally been used as a stabilizer. However, use of the metallic soap alone provides insufficient heat stability of the resin composition in producing a film by calendering, causing discoloration or decomposition of the resin composition. Even if the metallic soap is compounded in larger amounts in order to overcome this disadvantage, blooming or bleeding occurs, resulting in lowering the adhesive force of the pressure-sensitive adhesive to the backing film.

In view of the above, according to the present invention, a combination of at least one metallic soap selected from the group consisting of fatty acid calcium, fatty acid zinc and fatty acid barium, and hydrotalcite is used as the stabilizer. Of those metallic soaps is preferably used particularly a combination of fatty acid calcium and fatty acid zinc, which exhibits a high stabilization effect due to the synergistic effect when used as a combination (hereinafter referred to as a "Ca—Zn type stabilizers").

The fatty acid component of the metallic soap includes generally saturated or unsaturated fatty acids having 12 to 20 carbon atoms, such as lauric acid, stearic acid, ricinolic acid, etc.

Examples of the metallic soap preferably include calcium laurate, calcium stearate, calcium ricinolate, zinc laurate, zinc ricinolate, zinc stearate, barium laurate, barium stearate, barium ricinolate.

Hydrotalcite has the functions of not only imparting a heat stability required in the resin composition in the calendering, but also imparting a resistance to oxidation or decomposition to the film during use or storage, so that a life of the film can be prolonged. However, if hydrotalcite is used alone as the stabilizer, the heat stability of the resin composition in calendering the resin composition greatly deteriorates, regardless of the compounding amount thereof, resulting in discoloration or decomposition of the resin. As a result, the resin composition cannot be formed into a film.

Hydrotalcite is generally a non-stoichiometric, basic aluminum magnesium carbonate represented by the following compositional formula

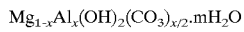

$$Mg_{1-x}Al_x(OH)_2(CO_3)_{x/2} \cdot mH_2O$$

wherein x is generally within the range of $0<x\leq0.33$, and m is generally within the range of $0\leq m\leq0.5$, and is a commercially available product (Sekkai and Sekko (Lime and Gypsum), vol. 187, pages 47–53 (1983)).

The amount of at least one metallic soap selected from the group consisting of fatty acid calcium, fatty acid zinc and fatty acid barium, used as the stabilizer in the present invention is not particularly limited, and an appropriate amount thereof is used. However, the amount of at least one metallic soap compounded is preferably within the range of about 0.5 and about 2.5 parts by weight per 100 parts by weight of the vinyl chloride polymer. If the amount of the metallic soap compounded is less than about 0.5 part by weight per 100 parts by weight of the vinyl chloride polymer, even if the metallic soap is used in combination with hydrotalcite as the stabilizer, the resin composition may lack its heat stability in calendering. On the other hand, if the amount of the metallic soap compounded is more than about 2.5 parts by weight per 100 parts by weight of the vinyl chloride polymer, blooming or bleeding may be caused, resulting in decrease of the adhesive force of the pressure-sensitive adhesive to the backing film.

Hydrotalcite used in combination with the metallic soap as the stabilizer in the present invention is used in an amount of about 0.1 to about 1.0 part by weight per 100 parts by weight of the vinyl chloride polymer. If the amount of hydrotalcite compounded is less than about 0.1 part by weight per 100 parts by weight of the vinyl chloride polymer, the resin composition lacks its heat stability in calendering, and discoloration of the resin composition is caused. On the other hand, if the amount of hydrotalcite compounded is more than about 1.0 part by weight per 100 parts by weight of the vinyl chloride polymer, coloration undesirably occurs due to hydrotalcite.

Thus, according to the present invention, a film comprising a vinyl chloride composition having compounded therewith the polyester plasticizer as the plasticizer and a mixture of the metallic soap and hydrotalcite as the stabilizer is used as the backing film for the pressure-sensitive adhesive sheet for skin adhesion. Such a backing film has an advantage from the standpoint of production in that it has excellent heat stability during forming a film from the resin composition by calendering, and undesirable coloration or the like does not occur. Further, the pressure-sensitive adhesive sheet for skin adhesion comprising the backing film thus obtained and the pressure-sensitive adhesive layer for skin adhesion provided thereon is advantageous in that since the plasticizer does not migrate into the pressure-sensitive adhesive layer, the adhesive force of the pressure-sensitive adhesive does not greatly decrease even with the lapse of long term, and the initial adhesive force is substantially maintained.

According to the present invention, the backing film for the pressure-sensitive adhesive sheet for skin adhesion may contain conventional stabilizers together with the above-described stabilizers, if desired, so long as the conventional stabilizers do not migrate from the backing film into the pressure-sensitive adhesive layer or if migrated they do not decrease the adhesive force of the pressure-sensitive adhesive. Examples of such conventional stabilizers include organic phosphite-based stabilizers. Further, according to the present invention, the backing film for the pressure-sensitive adhesive sheet for skin adhesion may contain various additives conventionally compounded with the vinyl chloride resin, for example, coloring materials, light stabilizers, antioxidants, ultraviolet absorbents, modifiers, fillers, flame retardants, antistatic agents, mildew-proofing agents and lubricants, if desired.

The backing film for the pressure-sensitive adhesive sheet for skin adhesion according to the present invention preferably has a thickness within the range of about 40 to about 100 μm such that when the pressure-sensitive adhesive sheet for skin adhesion is adhered to the skin, the backing film is well adaptable to the skin and well follows the skin, so that the user has no uncomfortable feeling.

According to the preferred embodiment of the present invention, the backing film for the pressure-sensitive adhesive sheet for skin adhesion can be obtained such that the resin composition comprising the vinyl chloride polymer having compounded therewith the polyester plasticizer having a number average molecular weight of about 1,500 to about 3,000, the stabilizer comprising at least one metallic soap selected from the group consisting of fatty acid calcium, fatty acid zinc and fatty acid barium, hydrotalcite, and if necessary, the above-described additives is molded into a film by calendering. Since the resin composition contains the polyester plasticizer as the plasticizer and also a mixture of the metallic soap and hydrotalcite as the stabilizer, the resin composition has excellent heat stability during calendering, and as a result, undesirable coloration or the like does not occur.

The pressure-sensitive adhesive sheet for skin adhesion according to the present invention can be obtained by providing the pressure-sensitive adhesive layer for skin adhesion on one side of the above-described backing film.

The pressure-sensitive adhesive which can be used in the present invention includes conventional acrylic pressure-sensitive adhesives and natural rubber pressure-sensitive adhesives, and there can be also used without any particular limitation any optional pressure-sensitive adhesives that have less skin irritation and can be used as medical pressure-sensitive adhesives, such as synthetic rubber pressure-sensitive adhesives, silicone pressure-sensitive adhesives and vinyl ether pressure-sensitive adhesives.

Of various pressure-sensitive adhesives, acrylic pressure-sensitive adhesives are preferably used in the present invention from the standpoint of a dermal pathology that it causes less allergy to skin.

Of the acrylic pressure-sensitive adhesives, acrylic pressure-sensitive adhesives comprising an acrylic copolymer are preferably used. The acrylic copolymer is obtained by copolymerizing an alkyl acrylate having 4 to 12 carbon atoms in the alkyl moiety which gives a polymer having a low glass transition temperature, such as 2-ethylhexyl acrylate or isononyl acrylate, as the main comonomer component, and optionally a vinyl ester, such as an alkyl (meth)acrylate having 1 to 3 carbon atoms in the alkyl moiety (e.g., methyl (meth)acrylate, ethyl (meth)acrylate or the like), vinyl acetate or N-methyl-2-pyrrolidone, as a component which gives a cohesive force, or a polar monomer having a polar group such as a hydroxyl group and/or a carboxyl group, such as (meth) acrylic acid or hydroxyalkyl (meth) acrylate having an alkyl group containing 2 to 10 carbon atoms in the hydroxyl moiety (e.g., hydroxyethyl ester, hydroxypropyl ester or the like), as a component which gives a cohesive force and also a crosslinking site.

Use of polar monomers having a hydroxyl group and/or a carboxyl group or the like polar groups is preferred since the resultant acrylic pressure-sensitive adhesive contains a hydroxyl group and/or a carboxyl group or the like polar groups so that it has excellent adhesive force to the backing film. Those comonomers are copolymerized in an appropriate organic solvent such as aliphatic hydrocarbon, alicyclic hydrocarbon, aromatic hydrocarbon, or aliphatic carboxylic acid ester, more specifically in ethyl acetate or toluene to produce an organic solvent type acrylic pressure-sensitive adhesive.

However, the pressure-sensitive adhesive for skin adhesion according to the present invention is not limited to the above-described organic solvent type pressure-sensitive adhesive, and is used in any form such as an emulsion type or a hot melt type. Those pressure-sensitive adhesives may be used alone or as mixtures of two or more thereof. The pressure-sensitive adhesive layer has a thickness of generally about 20 to about 80 $\mu$m, and preferably about 30 to about 60 $\mu$m, from the viewpoint of sufficient adhesion to the skin.

If desired, a crosslinking agent may be compounded with the pressure-sensitive adhesive. Examples of the crosslinking agent include modified polyisocyanates such as tolylene-diisocyanate trimethylol propane adduct and tris (2,3-epoxypropyl) isocyanurate, and organometallic compounds called chelater, such as aluminum tris(ethyl acetoacetate). A small amount, e.g., 0.05 to 1% by weight based on the weight of the composition, of the crosslinking agent is compounded with the pressure-sensitive adhesive, and such a pressure-sensitive adhesive is coated on one side of the backing film and dried, and then, if desired, heated to crosslink the acrylic pressure-sensitive adhesive, thereby the adhesive force of the pressure-sensitive adhesive can be controlled.

According to the present invention, prior to forming the pressure-sensitive adhesive layer for skin adhesion on one side of the backing film, the surface of the backing film, to which the pressure-sensitive adhesive is applied, maybe subjected to a corona discharge treatment or coated with the conventional various primers, thereby increasing wettability or anchoring effect between the backing film and the pressure-sensitive adhesive.

The pressure-sensitive adhesive layer is formed on one side of the backing film by directly coating a solution of the pressure-sensitive adhesive on the backing film and drying, or by melting a hot-melt pressure-sensitive adhesive and then directly coating the same on the backing film by an extruder. However, in order to prevent unnecessary elongation or curl of the backing film, it is preferable to use a so-called transfer method comprising previously forming the pressure-sensitive adhesive layer on one side of a release sheet by an appropriate method, laminating the backing film on this pressure-sensitive adhesive layer, and transferring the pressure-sensitive adhesive layer onto the backing film.

The pressure-sensitive adhesive sheet for skin adhesion according to the present invention can be used as a dressing, a bandage or the like, and also can be made as a first-aid adhesive plaster by providing an absorbent pad for protecting a wound portion, such as a cloth (e.g., gauze) or a sponge pad, at a central region on the surface of the pressure-sensitive adhesive layer.

EXAMPLES

The present invention is explained in more detail by referring to the following examples, but the invention is not limited thereto. In the examples and comparative examples, the Ca—Zn type stabilizer used is M series manufactured by Dainippon Ink & Chemicals Inc., and the polyester stabilizer used is POLYCIZER W, a product of Dainippon Ink & Chemicals Inc.

Example 1

Ca—Zn type stabilizer, hydrotalcite (ALKAMIZER I, a product of Kyowa Kagaku Kogyo K.K.; in the formula described before, x=0.33, m=0.50) and a polyester plasticizer having various number average molecular weight (POLYCIZER W, a product of Dainippon Ink & Chemicals Inc.) were blended with polyvinyl chloride (average degree of polymerization: 1,300) as shown in Table 1 below, and the resulting blend was sufficiently mixed with a Henschel mixer, and then kneaded with a closed kneader. The resulting mixture was passed through a strainer, and using a reverse L type four-roll calendering apparatus (roll surface temperature: 180° C.), a backing film for a pressure-sensitive adhesive sheet having a thickness of 70 $\mu$m comprising a vinyl chloride resin was obtained.

Separately, 0.02 part by weight (solids content) of a modified polyisocyanate (CORONATE L, a product of Nippon Polyurethane Kogyo K.K.) was compounded with 100 parts by weight of a commercially available acrylic pressure-sensitive adhesive (AR-2045, a product of Rikidyne K.K.) to prepare a pressure-sensitive adhesive. This pressure-sensitive adhesive was coated on the above-described backing film in a dry thickness of 35 $\mu$m.

A sample of a pressure-sensitive adhesive sheet for skin adhesion comprising a backing film having provided on one side thereof a pressure-sensitive adhesive layer was allowed to stand at room temperature (23° C.), or allowed to stand at 70° C. for 15 days to conduct accelerated deterioration. The sample thus treated was adhered to a stainless steel plate in a width of 19 mm, and an adhesive force of the sample before measurement and after allowing to stand at 23° C. for 24 hours was measured at a peel angle of 180° and a tensile speed of 300 mm/min using a constant speed extension tensile tester according to JIS Z 0237. The adhesive force with the lapse of time of the sample was evaluated by retention of a peel force after accelerated deterioration to an ordinary peel force. The results obtained are shown in Table 1 below.

Examples 2 and 3

A backing film was obtained in the same manner as in Example 1 except that a resin composition as shown in Table 1 was prepared. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

Example 4

A backing film was obtained in the same manner as in Example 1 except that the compounding amount of hydrotalcite was changed as shown in Table 1. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

Comparative Example 1

A backing film was obtained in the same manner as in Example 1 except that a resin composition was prepared using a polyester plasticizer having a number average molecular weight of 1,000 (POLYCIZER W-1000, a product of Dainippon Ink & Chemicals Inc.) as shown in Table 1. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

Comparative Example 2

A backing film was obtained in the same manner as in Example 1 except that a resin composition was prepared using dioctyl phthalate as a plasticizer in place of the polyester plasticizer as shown in Table 1. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

Comparative Example 3

A backing film was obtained in the same manner as in Example 1 except that a resin composition was prepared by compounding only Ca—Zn type stabilizer as a stabilizer, and not using hydrotalcite as shown in Table 1. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

Comparative Example 4

A backing film was obtained in the same manner as in Example 1 except that a resin composition was prepared using a polyester plasticizer having a number average molecular weight of 2,300 (POLYCIZER W-2310, a product of Dainippon Ink & Chemicals Inc.) as a plasticizer and also using a combination of Ca—Zn type stabilizer and epoxidized soybean oil (W-100EL, a product of Dainippon Ink & Chemicals Inc.) as a stabilizer as shown in Table 1. The pressure-sensitive adhesive as used in Example 1 was coated on the backing film obtained to prepare a sample of a pressure-sensitive adhesive sheet for skin adhesion. The ordinary peel force and the retention of a peel force after accelerated deterioration were determined on the sample in the same manner as in Example 1. The results obtained are shown in Table 1 below.

TABLE 1

| | Example 1 | Example 2 | Example 3 | Example 4 | C. Example 1 | C. Example 2 | C. Example 3 | C. Example 4 |
|---|---|---|---|---|---|---|---|---|
| Formulation of resin composition (parts by weight) | | | | | | | | |
| Polyvinyl chloride | 100 | 100 | 100 | 100 | 100 | 100 | 100 | 100 |
| Ca—Zn type stabilizer | 1.0 | 1.0 | 1.0 | 1.0 | 1.0 | 1.0 | 1.0 | 1.0 |
| Hydrotalcite | 0.3 | 0.3 | 0.3 | 0.2 | 0.3 | 0.3 | | |
| Epoxidized soybean oil[1] | | | | | | | | 3.0 |
| Polyester plasticizer[2] | | | | | | | | |
| W-1000 (M.W.: 1,000) | | | | | 40 | | | |
| W-1600 (M.W.: 1,600) | | | 44 | | | | | |
| W-2050 (M.W.: 2,000) | | 48 | | | | | | |
| W-2310 (M.W.: 2,300) | 50 | | | 50 | | | 50 | 47 |
| Dioctyl phthalate | | | | | | 40 | | |
| Adhesive force with the lapse of time | | | | | | | | |
| Ordinary peel force (gf/19 mm width) | 930 | 910 | 900 | 910 | 820 | 810 | 800 | 820 |
| Retention of peel force after accelerated deterioration (%) | 88 | 87 | 81 | 85 | 60 | 40 | 65 | 41 |

Notes:
[1]W-100EL, a product of Dainippon Ink & Chemicals Inc.
[2]POLYCIZER W, a product of Dainippon Ink & Chemicals Inc.
M.W.: Molecular weight
C. Example: Comparative Example

Reference Example 1

100 Parts by weight of 2-ethylhexyl acrylate, 40 parts by weight of vinyl acetate and 5 parts by weight of acrylic acid were copolymerized in ethyl acetate to obtain a solution of an acrylic pressure-sensitive adhesive A having a solids content concentration of 35 wt %.

Reference Example 2

65 Parts by weight of isononyl acrylate and 35 parts by weight of vinyl acetate were copolymerized in ethyl acetate to obtain a solution of an acrylic pressure-sensitive adhesive B having a solids content concentration of 35 wt %.

Reference Example 3

100 Parts by weight of natural rubber, 100 parts by weight of styrene-butadiene copolymer, 170 parts by weight of terpene resin, 100 parts by weight of low number average molecular weight polyisoprene (number average molecular weight: 30,000) and 3 parts by weight of bisphenol as a stabilizer were uniformly mixed in toluene to obtain a solution of a rubber pressure-sensitive adhesive C having a solids content concentration of 25 wt %.

Example 5

1.0 Part by weight of Ca—Zn type stabilizer, 0.7 part by weight of hydrotalcite (ALKAMIZER I, a product of Kyowa Kagaku Kogyo K.K.) and a polyester plasticizer having a number average molecular weight of 2,300 (POLYCIZER W-2310, a product of Dainippon Ink & Chemicals Inc.) were compounded with 100 parts by weight of polyvinyl chloride (average degree of polymerization: 1,300), and the resulting blend was sufficiently mixed with a Henschel mixer, and then kneaded with a closed kneader. The resulting mixture was passed through a strainer, and using a reverse L type four-roll calendering apparatus (roll surface temperature: 180° C.), a backing film for a pressure-sensitive adhesive sheet having a thickness of 70 μm comprising a vinyl chloride resin was obtained.

Separately, the solution of a pressure-sensitive adhesive A prepared in Reference Example 1 above was coated on a release sheet, one surface of which having been subjected to release treatment with a silicone resin, in a dry thickness of about 40 μm, and dried to form a pressure-sensitive adhesive layer. The backing film obtained above was laminated on this pressure-sensitive adhesive layer, and the pressure-sensitive adhesive layer was transferred to the backing film, thereby obtaining a pressure-sensitive adhesive sheet for skin adhesion.

A sample having a width of 19 mm and a length of 150 mm was prepared from the pressure-sensitive adhesive sheet for skin adhesion thus obtained. The sample was adhered to a phenolic resin plate, and an initial value of an adhesive force of the pressure-sensitive adhesive sheet and an adhesive force of the pressure-sensitive adhesive sheet after allowing to stand the same in a constant temperature bath at 50° C. or 70° C. for 30 days were measured. The adhesive force was measured by conducting a 180° peeling test at a tensile speed of 300 mm/min using a constant speed extension tensile tester under the conditions of temperature of 23±2° C. and a relative humidity of 65±15% according to JIS Z 0237. The results obtained are shown in Table 2.

Examples 6 and 7

A layer comprising each of the pressure-sensitive adhesives B and C prepared in Reference Examples 2 and 3 was formed on the backing film prepared in Example 5 in a thickness of about 40 μm to obtain the respective pressure-sensitive adhesive sheet for skin adhesion. The adhesive force of those pressure-sensitive adhesive sheets for skin adhesion was measured in the same manner as in Example 5. The results obtained are shown in Table 2 below.

Comparative Example 5

A pressure-sensitive adhesive layer was formed on the backing film prepared in Comparative Example 4 in the same manner as in Example 5 to obtain a pressure-sensitive adhesive sheet for skin adhesion. The adhesive force of the pressure-sensitive adhesive sheet for skin adhesion was measured in the same manner as in Example 5. The results obtained are shown in Table 2 below.

TABLE 2

|  | Example 5 | Example 6 | Example 7 | Comparative Example 5 |
|---|---|---|---|---|
| Pressure-sensitive adhesive | A | B | C | A |
| Adhesive force (gf/19 mm width) | | | | |
| Initial value | 850 | 720 | 730 | 810 |
| 50° C. × 30 days | 780 | 680 | 700 | 410 |
| 70° C. × 30 days | 720 | 650 | 680 | 250 |

Example 8

The pressure-sensitive adhesive sheet for skin adhesion prepared in Example 5 was allowed to stand at 50° C. for 30 days, and then cut into a sample having a width of 19 mm and a length of 72 mm. This sample was adhered on the second joint of the fingers of ten subjects for 8 hours. After conducting an ordinary kitchen work, the adhesion property of the sheet to the skin and the adhesive remaining on the skin when peeling the adhesive sheet from the fingers were examined.

The evaluation standard was conducted using the five grades of 5: Good, 3: Moderate, and 1: Poor. As a result, the evaluation of the adhesive property to the skin was 5, and the evaluation of the adhesive remaining was 4.

Comparative Example 6

The pressure-sensitive adhesive sheet for skin adhesion prepared in Comparative Example 5 was allowed to stand at 50° C. for 30 days, and cut into a test piece having a width of 19 mm and a length of 72 mm. The adhesion property of the sheet to the skin and the adhesive remaining on the skin when peeling the adhesive sheet from the fingers were examined in the same manner as in Example 8. The evaluation of the adhesive property to the skin was 2 (the adhesive sheet peeled during adhering in three test persons), and the evaluation of the adhesive remaining was 5.

Example 9

Ca—Zn type stabilizer, hydrotalcite (ALKAMIZER I, a product of Kyowa Kagaku Kogyou K.K.), and a polyester plasticizer having a number average molecular weight of 2,300 (POLYCIZER W-2300, a product of Dainippon Ink & Chemicals Inc.) were compounded with a polyvinyl chloride (average degree of polymerization: 1,300) as shown in Table 3, and the resulting blend was sufficiently mixed with a Henschel mixer to prepare a resin composition. This resin composition was subjected to heat resistance test of kneading the composition for 15 minutes using rolls having a surface temperature of 180° C. to examine the degree of discoloration (ΔE). The results obtained are shown in Table 3 below. If the ΔE is smaller than 1.0, it can be judged that the resin composition has the calendering property. Further, the calendering property was examined on the resin composition using a plast mill (190° C.×60 rpm). If decomposition time is 15 minutes or more, it can be judged that the resin composition has the calendering property.

Comparative Examples 7 to 9

The resin compositions were prepared in the same manner as in Example 9 except for preparing the resin compositions as shown in Table 3, and the calendering property thereof was examined. The results obtained are shown in Table 3 below. The resin compositions of Comparative Examples 7 and 8 do not have the calendering property. The resin composition of Comparative Example 9 can provide a film by calendering, but since the obtained backing film contains an epoxidized soybean oil in place of hydrotalcite, the pressure-sensitive adhesive sheet for skin adhesion obtained by coating the pressure-sensitive adhesive on the backing film is decreased in adhesive force with the passage of time.

Example 10

First-aid adhesive plasters were prepared by attaching an absorbent pad made of gauze (15 mm×36 mm) at a central region on the surface of the pressure-sensitive adhesive layer of the pressure-sensitive adhesive sheet for skin adhesion produced in Examples 1 to 9 cut to a size of 19 mm×72 mm.

TABLE 3

|  | Example 9 | Comparative Example 7 | Comparative Example 8 | Comparative Example 9 |
|---|---|---|---|---|
| Resin composition formulation (parts by weight) |  |  |  |  |
| Polyvinyl chloride | 100 | 100 | 100 | 100 |
| Ca—Zn type stabilizer | 1.0 | 1.0 |  | 1.0 |
| Hydrotalcite | 0.3 |  | 0.3 |  |
| Epoxidized soybean oil[1)] |  |  |  | 3.0 |
| Polyester plasticizer[2)] | 50 | 50 | 50 | 47 |
| Calendering property |  |  |  |  |
| Discoloration (ΔE) | 0.5 | 1.5 | 9.5 | 0.5 |
| Decomposition time (min) | 17 | 11 | 4 | 17 |

Notes:
[1)]W-100EL, a product of Dainippon Ink & Chemicals Inc.
[2)]POLYCIZER W-2310 (molecular weight: 2,300), a product of Dainippon Ink & Chemicals Inc.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A flexible pressure-sensitive adhesive sheet for skin adhesion, comprising a flexible backing film and a pressure-sensitive adhesive layer, with an absorbent pad provided on a central region thereof, for skin adhesion, formed on one side of the backing film, wherein the improvement for reducing the loss in adhesive force of the sheet to human skin over time comprises the adhesive sheet comprising a flexible backing film which consists essentially of:
    100 parts by weight of a flexible vinyl chloride polymer;
    about 40 to about 70 parts by weight of polyester plasticizer having a number average molecular weight of about 1,500 to about 3,000;
    a stabilizing effective amount of about 0.5 to about 2.5 parts by weight per 100 part by weight of the vinyl chloride polymer of a stabilizer consistig essentially of at least one metallic soap selected from the group consisting of fatty acid calcium, fatty acid zinc and fatty acid barium; and
    about 0.1 to about 1.0 part by weight of hydrotalcite.

2. The pressure-sensitive adhesive sheet for skin adhesion as claimed in claim 1, wherein the vinyl chloride polymer is at least one polymer selected from a polymer of vinyl chloride alone and copolymers of vinyl chloride and an ethylenically unsaturated hydrocarbon having 2 to 4 carbon atoms.

3. The pressure-sensitive adhesive sheet for skin adhesion as claimed in claim 2, wherein the vinyl chloride polymer is at least one polymer selected from the group consisting of polyvinyl chloride and vinyl chloride/ethylene copolymers and vinyl chloride/vinyl acetate copolymer.

4. The pressure-sensitive adhesive sheet for skin adhesion as claimed in claim 1, wherein the vinyl chloride polymer has an average degree of polymerization of about 500 to about 1,500.

5. The pressure-sensitive adhesive sheet for skin adhesion as claimed in claim 1, wherein the polyester plasticizer comprises a polyester obtained from an aliphatic or aromatic dicarboxylic acid having 2 to 10 carbon atoms and a glycol having 2 to 10 carbon atoms.

6. The pressure-sensitive adhesive sheet for skin adhesion as claimed in claim 1, wherein the metallic soap is a combination of a fatty acid calcium and a fatty acid zinc.

7. The pressure-sensitive adhesive sheet for skin adhesion as claimed in claim 6, wherein the fatty acid in the metallic soap is a saturated or unsaturated fatty acid having 12 to 20 carbon atoms.

8. The pressure-sensitive adhesive sheet for skin adhesion as claimed in claim 1, wherein the metallic soap is in an amount of about 0.5 to about 2.5 parts by weight per 100 parts by weight of the vinyl chloride polymer.

9. The pressure-sensitive adhesive sheet for skin adhesion as claimed in claim 1, wherein the pressure-sensitive adhesive is an acrylic pressure-sensitive adhesive.

10. The pressure-sensitive adhesive sheet for skin adhesion as claimed in claim 9, wherein the acrylic pressure-sensitive adhesive comprises a polymer comprising an alkyl acrylate having 4 to 12 carbon atoms in the alkyl moiety as a main monomer component.

11. The pressure-sensitive adhesive sheet for skin adhesion as claimed in claim 10, wherein the acrylic pressure-sensitive adhesive further comprises at least one vinyl ester selected from the group consisting of alkyl (meth)acrylates having 1 to 3 carbon atoms in the alkyl moiety, vinyl acetate and N-methyl-2-pyrrolidone.

12. The pressure-sensitive adhesive sheet for skin adhesion as claimed in claim 10, wherein the acrylic pressure-sensitive adhesive comprises an acrylic pressure-sensitive adhesive that contains at least one of a hydroxyl group and a carboxyl group.

13. The pressure-sensitive adhesive sheet for skin adhesion as claimed in claim 12, wherein the acrylic pressure-sensitive adhesive comprises a copolymer comprising an alkyl acrylate ester as a main monomer component and an hydroxyalkyl (meth) acrylate or (meth)acrylic acid as a comonomer copolymerizable therewith.

14. A process for applying a pressure sensitive adhesive sheet to a human skin, wherein the loss in adhesive force of a pressure sensitive adhesive layer of the sheet to human skin over time is reduced, comprising applying to human skin a pressure sensitive adhesive sheet comprising
    a flexible backing film and a pressure-sensitive adhesive layer for skin adhesion formed on one side of the backing film, wherein the flexible backing film consists essentially of:
    100 parts by weight of a flexible vinyl chloride polymer;
    about 40 to about 70 parts by weight of a polyester plasticizer having a number average molecular weight of about 1,500 to about 3,000;

a stabilizing effective amount of about 0.5 to about 2.5 parts by weight per 100 parts by weight of the vinyl chloride polymer of a stabilizer consisting essentially of at least one metallic soap selected from the group consisting of fatty acid calcium, fatty acid zinc and fatty acid barium; and about 0.1 to about 1.0 part by weight of hydrotalcite, to the skin with the pressure sensitive adhesive layer being in contact with the skin.

15. A process for applying a pressure-sensitive adhesive sheet as in claim 14, wherein the vinyl chloride polymer is at least one polymer selected from a polymer of vinyl chloride alone and copolymers of vinyl chloride and an ethylenically unsaturated hydrocarbon having 2 to 4 carbon atoms.

16. A process for applying a pressure-sensitive adhesive sheet as in claim 14, wherein the vinyl chloride polymer is at least one polymer selected from the group consisting of polyvinyl chloride and vinyl chloride/ethylene copolymers and vinyl chloride/vinyl acetate copolymer.

17. A process for applying a pressure-sensitive adhesive sheet as in claim 14, wherein the vinyl chloride polymer has an average degree of polymerization of about 500 to about 1,500.

18. A process for applying a pressure-sensitive adhesive sheet as in claim 16, wherein the polyester plasticizer comprises a polyester obtained from an aliphatic or aromatic dicarboxylic acid having 2 to 10 carbon atoms and a glycol having 2 to 10 carbon atoms.

19. A process for applying a pressure-sensitive adhesive sheet as in claim 16, wherein the metallic soap is a combination of a fatty acid calcium and a fatty acid zinc.

20. A process for applying a pressure-sensitive adhesive sheet as in claim 16, wherein the fatty acid in the metallic soap is a saturated or unsaturated fatty acid having 12 to 20 carbon atoms.

21. A process for applying a pressure-sensitive adhesive sheet as in claim 16, wherein the vinyl chloride polymer, wherein the metallic soap is in an amount of about 0.5 to about 2.5 parts by weight per 100 parts by weight of the vinyl chloride polymer.

22. A process for applying a pressure-sensitive adhesive sheet as in claim 14, wherein the pressure-sensitive adhesive is an acrylic pressure-sensitive adhesive.

23. A process for applying a pressure-sensitive adhesive sheet as in claim 14, wherein the acrylic pressure-sensitive adhesive comprises a polymer comprising an alkyl acrylate having 4 to 12 carbon atoms in the alkyl moiety as a main monomer component.

24. A process for applying a pressure-sensitive adhesive sheet as in claim 14, wherein the acrylic pressure-sensitive adhesive further comprises at least one vinyl ester selected from the group consisting of alkyl (meth)acrylates having 1 to 3 carbon atoms in the alkylmoiety, vinyl acetate and N-methyl-2-pyrrolidone.

25. A process for applying a pressure-sensitive adhesive sheet as in claim 14, wherein the acrylic pressure-sensitive adhesive comprises an acrylic pressure-sensitive adhesive that contains at least one of a hydroxyl group and a carboxyl group.

26. A process for applying a pressure-sensitive adhesive sheet as in claim 14, wherein the acrylic pressure-sensitive adhesive comprises a copolymer comprising an alkyl acrylate ester as a main monomer component and an hydroxyalky (meth) acrylate or (meth) acrylic acid as a comonomer copolymerizable therewith.

* * * * *